US005612307A

United States Patent [19]
Chambers et al.

[11] Patent Number: 5,612,307
[45] Date of Patent: Mar. 18, 1997

[54] DETERGENT COMPOSITIONS CONTAINING SEPARATE STRIPES OF SURFACE ACTIVE AGENTS AND BENEFIT AGENT

[75] Inventors: John G. Chambers, Bromborough; Ailsa P. H. Grieveson, Heswall; Margaret Jobling, Bebington, all of Great Britain

[73] Assignee: Lever Brothers Company, Division of Conopco, Inc., New York, N.Y.

[21] Appl. No.: 475,145

[22] Filed: Jun. 7, 1995

[30] Foreign Application Priority Data

Jul. 19, 1994 [GB] United Kingdom ............ 9414573

[51] Int. Cl.$^6$ .............. C11D 3/16; C11D 3/18; C11D 3/20; A61K 7/00
[52] U.S. Cl. .......... 510/406; 510/119; 510/121; 510/122; 510/130; 510/158; 510/159; 510/437; 424/401; 514/844
[58] Field of Search ............... 252/90, 174.15, 252/DIG. 13, DIG. 14; 424/401; 514/844; 510/119, 121, 122, 130, 158, 159, 406, 437

[56] References Cited

U.S. PATENT DOCUMENTS

| | | | |
|---|---|---|---|
| 3,533,955 | 10/1970 | Pader et al. | 253/153 |
| 4,777,089 | 10/1988 | Takizawa et al. | 428/402.22 |
| 4,981,845 | 1/1991 | Pereira | 514/557 |
| 5,059,414 | 10/1991 | Daual et al. | 424/70 |
| 5,455,035 | 10/1995 | Guerrerd et al. | 424/401 |

FOREIGN PATENT DOCUMENTS

| | | |
|---|---|---|
| 0419164 | 3/1991 | European Pat. Off. . |
| 0468703 | 1/1992 | European Pat. Off. . |
| 956377 | 4/1964 | United Kingdom . |
| 2246363 | 1/1992 | United Kingdom . |
| 93/09761 | 5/1993 | WIPO . |
| 94/03152 | 2/1994 | WIPO . |
| 94/04130 | 3/1994 | WIPO . |
| 9522311 | 8/1995 | WIPO . |

*Primary Examiner*—Paul Lieberman
*Assistant Examiner*—Lorna M. Douyon
*Attorney, Agent, or Firm*—Ronald A. Koatz

[57] ABSTRACT

An aqueous liquid cleansing and moisturising composition comprising a surface active agent and a benefit agent in which the surface active agent and benefit agent are separate but combinedly dispensable from a single packaging means in a predetermined ratio as discrete domains. Separating the benefit agent from the surface active agent results in improved deposition of the benefit agent.

8 Claims, No Drawings

5,612,307

DETERGENT COMPOSITIONS CONTAINING SEPARATE STRIPES OF SURFACE ACTIVE AGENTS AND BENEFIT AGENT

FIELD OF THE INVENTION

The present invention relates to detergent compositions suitable for topical application for cleansing and improving the condition of the human body, particularly for moisturising the skin, hair, nails and other epithelial tissues, including the mucosae. In particular, it relates to compositions which are formulated to give mild cleansing and conditioning of the skin.

DISCUSSION OF RELATED ART

Compositions formulated to cleanse the skin are well known. It is also known to formulate products which provide both a cleansing and a moisturising benefit.

For example WO 90/13283 discloses a composition comprising an acyl ester of an isethionic acid salt, a long chain fatty acid, a moisturiser component and, optionally, soap.

One of the problems which may be encountered with such dual purpose compositions is that they contain an insufficient level of moisturiser component or an insufficient amount is deposited on use.

We have found a way of formulating such compositions such that they can deliver effective moisturising, conditioning and/or protection of the skin.

Another problem associated with such dual cleansing and moisturising compositions is instability. According to WO 94/03152, concerned with shower gels comprising a non-soap detergent, silicone oil and cationic polymers, the maximum average droplet size of the silicone oil than can be used is 2 microns, if product stability is to be maintained.

SUMMARY OF THE INVENTION

We have now found the stability of a dual cleansing and moisturising product and delivery and deposition of the moisturising agent can be improved by providing a composition in which the cleansing and moisturising components are separate but combinedly dispensable from a packaging means as discrete domains.

Thus, according to the invention there is provided an aqueous liquid cleansing and moisturising composition comprising:
  a) a surface active agent selected from anionic, nonionic, zwitterionic and cationic, surface active agents, soap and mixtures thereof; and
  b) a benefit agent;
wherein the benefit agent and surface active agent are separate but combinedly dispensable from a single packaging means in a predetermined ratio as discrete domains, the domains having one dimension of at least about 1000 microns.

An advantage of the present invention is that it leads to improved deposition of benefit agents from a surface active agent containing aqueous liquid composition during use. The surface active agent and benefit agent are separated in the composition, i.e. they do not directly contact one another in the composition. This avoids adverse interactions which may occur between these two components and resulting in ineffective deposition of the benefit agent.

DETAILED DESCRIPTION OF THE INVENTION

The surface active agent and benefit agent are dispensable from a single packaging means in a predetermined ratio according to the use for which composition is intended. An advantage of dispensing the surface active agent and benefit agent in combination is that it avoids the inconvenience of having to post mix the two components. This is particularly advantageous when the separate components of a composition need to be mixed in precise ratios in order to achieve the desired effect.

The discrete domains of the composition of the invention may be considered as separate stripes of surface active agents and of benefit agent.

The composition is suitable for cleansing and "moisturising", "conditioning" or "protection" of the skin. The benefit agent is included in the composition to moisturise, condition and/or protect the skin. By "benefit agent" is meant a substance that softens the skin (stratum corneum) and keeps it soft by retarding the decrease of its water content and/or protects the skin.

Preferred benefit agents include a) silicone oils, gums and modifications thereof such as linear and cyclic polydimethylsiloxanes, amino, alkyl alkylaryl and aryl silicone oils;

b) fats and oils including natural fats and oils such as jojoba, soyabean, rice bran, avocado, almond, olive, sesame, persic, castor, coconut, mink oils; cacao fat, beef tallow, lard; hardened oils obtained by hydrogenating the aforementioned oils; and synthetic mono, di and triglycerides such as myristic acid glyceride and 2-ethylhexanoic acid glyceride;

c) waxes such as carnauba, spermaceti, beeswax, lanolin and derivatives thereof;

d) hydrophobic plant extracts;

e) hydrocarbons such as liquid paraffins, petroleum jelly, microcrystalline wax, ceresin, squalene, squalane, and mineral oil;

f) higher fatty acids such as lauric, myristic, palmitic, stearic, behenic, oleic, linoleic linolenic, lanolic, isostearic and poly unsaturated fatty acids (PUPA) acids;

g) higher alcohols such as lauryl, cetyl, steryl, oleyl, behenyl, cholesterol and 2-hexadecanol alcohol;

h) esters Such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate for example lauryl lactate, alkyl citrate and alkyl tartrate;

i) essential oils such as fish oils, mentha, jasmine, camphor, white cedar, bitter orange peel, ryu, turpentine, cinnamon, bergamont, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, pinene, limonene and terpenoid oils;

j) lipids such as cholesterol, ceramides, sucrose esters and pseudo-ceramides as described in European Patent Specification No. 556 957;

k) vitamins such as vitamin A and E, and vitamin alkyl esters, including those vitamin C alkyl esters;

l) sunscreens such as octyl methoxyl cinnamate (Parsol MCX) and butyl methoxy benzoylmethane (Parsol 1789)

m) Phospholipids; and n) mixtures of any of the foregoing components.

Where adverse interactions between the benefit agent and surface active are likely to be particularly acute, the benefit agent may be incorporated in the compositions of the invention in a carrier.

Such benefit agents include lipids; alkyl lactates; sunscreens; esters such as isopropyl palmitate and isopropyl myristate; and vitamins. The carrier can, for example, be a silicone or hydrocarbon oil which is not solubilised/micellised by the surface active phase and in which the benefit agent is relatively soluble.

Particularly preferred benefit agents include silicone oils, gums and modification thereof; esters such as isopropyl palmitate and myristate and alkyl lactates.

The benefit agent can be provided in the form of an emulsion.

The benefit agent is preferably present in amount of from 0.1 to 50 wt %, most preferably from 4 to 25 wt %.

An advantage of the composition according to the invention is that, during use, it deposits benefit agent onto the skin at a level which results in a perceivable benefit. Without being bound by theory, it is believed the benefit agent is dispersed into large pools during dilution of the composition in use and these pools deposit readily onto the skin.

The surface active agent can be selected from any known surfactant suitable for topical application to the human body. Mild surfactants, i.e. surfactants which do not damage the stratum corneum, the outer layer of skin, are particularly preferred.

One preferred anionic detergent is fatty acyl isethionate of formula:

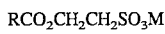
RCO$_2$CH$_2$CH$_2$SO$_3$M where R is an alkyl or alkenyl group of 7 to 21 carbon atoms and M is a solubilising cation such as sodium, potassium, ammonium or substituted ammonium. Preferably at least three quarters of the RCO groups have 12 to 18 carbon atoms and may be derived from coconut, palm or a coconut/palm blend.

Another preferred anionic detergent is alkyl ether sulphate of formula:

RO(CH$_2$CH$_2$O)$_n$SO$_3$M where R is an alkyl group of 8 to 22 carbon atoms, n ranges from 0.5 to 10 especially from 1.5 to 8, and M is a solubilising cation as before.

Other possible anionic detergents include alkyl glyceryl ether sulphate, sulphosuccinates, taurates, sarcosinates, sulphoacetates, alkyl phosphate, alkyl phosphate esters and acyl lactylate, alkyl glutamates and mixtures thereof.

Sulphosuccinates may be monoalkyl sulphosuccinates having the formula: R$^5$O$_2$CCH$_2$CH(SO$_3$M)CO$_2$M; and amido-MEA sulphosuccinates of the formula: R$^5$CONHCH$_2$CH$_2$O$_2$CCH$_2$CH(SO$_3$M)CO$_2$M; wherein R$^5$ ranges from C$_8$–C$_{20}$ alkyl, preferably C$_{12}$–C$_{15}$ alkyl and M is a solubilising cation.

Sarcosinates are generally indicated by the formula: R$^5$CON(CH$_3$)CH$_2$CO$_2$M, wherein R$^5$ ranges from C$_8$–C$_{20}$ alkyl, preferably C$_{12}$–C$_{15}$ alkyl and M is a solubilising cation.

Taurates are Generally identified by the formula: R$^5$CONR$^6$CH$_2$CH$_2$SO$_3$M, wherein R$^5$ ranges from C$_8$–C$_{20}$ alkyl, preferably C$_{12}$–C$_{15}$ alkyl, R$^6$ ranges from C$_1$–C$_4$ alkyl, and M is a solubilising cation.

Harsh surfactants such as primary alkane sulphonate or alkyl benzene sulphonate will generally be avoided.

Suitable nonionic surface active agents include alkyl polysaccharides, lactobionamides, ethyleneglycol esters, glycerol monoethers, polyhydroxyamides (glucamide), primary and secondary alcohol ethoxylates, especially the C$_8$–C$_{20}$ aliphatic alcohols ethoxylated with an average of from 1 to 20 moles of ethylene oxide per mole of alcohol.

If the surface active agent comprises soap, the soap is preferably derived from materials with a C$_8$ to C$_{22}$ substantially saturated carbon chain and, preferably, is a potassium soap with a C$_{12}$ to C$_{18}$ carbon chain.

Mixtures of any of the foregoing surface active agents may also be used.

The surface active agent is preferably present at a level of from 1 to 35 wt %, preferably 3 to 30 wt %.

It is also preferable that the composition includes from 0.5 to 15 wt % of a cosurfactant agent with skin-mildness benefits. Suitable materials are zwitterionic detergents which have an alkyl or alkenyl group of 7 to 18 carbon atoms and comply with an overall structural formula:

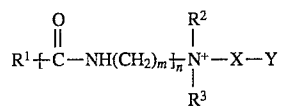

where R$^1$ is alkyl or alkenyl of 7 to 18 carbon atoms R$^2$ and R$^3$ are each independently alkyl, hydroxyalkyl or carboxyalkyl of 1 to 3 carbon atoms;

m is 2 to 4;

n is 0 or 1;

X is alkylene of 1 to 3 carbon atoms optionally substituted with hydroxyl; and

Y is —CO$_2$ or —SO$_3$.

Zwitterionic detergents within the above general formula include simple betaines of formula:

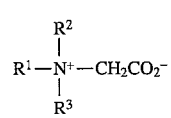

and amido betaines of formula:

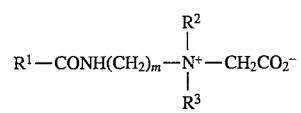

where m is 2 or 3.

In both formulae R$^1$, R$^2$ and R$^3$ are as defined previously. R$^1$ may, in particular, be a mixture of C$_{12}$ and C$_{14}$ alkyl groups derived from coconut so that at least half, preferably at least three quarters, of the group R$^1$ has 10 to 14 carbon atoms. R$^2$ and R$^3$ are preferably methyl.

A further possibility is a sulphobetaine of formula:

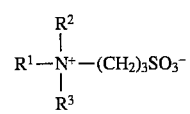

or $$R^1-CONH(CH_2)_m\overset{R^2}{\underset{R^3}{N^+}}-(CH_2)_3SO_3^-$$

where m is 2 or 3, or variants of these in which —(CH$_2$)$_3$SO$_3$— is replaced by $$-CH_2\overset{OH}{\underset{}{C}}HCH_2SO_3^-$$

R$^1$, R$^2$ and R$^3$ in these formulae are as defined previously.

A structurant may be added to the phase comprising the surface active agent. Suitable materials include swelling clays, for example laponite; fatty acids and derivatives thereof, in particular, fatty acid monoglyceride polyglycol ethers; cross-linked polyacrylates such as Carbopol (TM) (polymers available from Goodrich); acrylates and copolymers thereof; polyvinylpyrrolidone and copolymers thereof; polyethylene imines; salts such as sodium chloride and ammonium sulphate; sucrose esters; gellants; and mixtures thereof.

Of the clays, particularly preferred are synthetic hectorite (laponite) clay used in conjunction with an electrolyte salt capable of causing the clay to thicken. Suitable electrolytes include alkali and alkaline earth salts such as halides, ammonium salts and sulphates.

The surface active agent phase may also comprise a thickening agent, ie a material which maintains the viscosity of this phase as the shear rate thereof is increased during use. Suitable materials include cross-linked polyacrylates such as Carbopol (TM) (polymers available from Goodrich); natural gums including alginates, guar, xanthan and polysaccharide derivatives including carboxy methyl cellulose and hydroxypropyl guar; propylene glycols and propylene glycol oleates; salts such as sodium chloride and ammonium sulphate; glycerol tallowates; and mixtures thereof.

Thickeners may also be added to the benefit agent in order to achieve the required viscosity during use. Preferred thickeners for the benefit agent include fumed silica; polyethylene; alkyl silicone waxes; aluminium silicate; lanesterol; natural and synthetic waxes; fatty acids and derivatives thereof, in particular, fatty acid monoglyceride polyglycol ethers; higher fatty alcohols; petrolatum; narogel; polyammonium stearate; hydrotalcites; and mixtures thereof. Hydrotalcites are materials of general formula $$[M_mN_n(OH)_{2(m+n)}]^{n+}X^{x-}{}_{n/x}yH_2O$$

where

M is a divalent metal ion e.g. Mg$^{2-}$;

N is a trivalent metal ion e.g. Al$^{3+}$;

X is an exchangeable anion e.g CO$_3^-$, NO$_3^-$;

stearate, cinnimate;

m is the number of divalent metal ions; and n is the number of trivalent metal ions.

Whilst some materials can function as both a benefit agent and a thickener therefor, it will be appreciated than the benefit and thickening function cannot be provided by the same component. However, it will be understood that where the composition comprises two or more benefit agents one of said benefit agents may also function as a thickening agent.

Further examples of structurants and thickeners are given in the International Cosmetic Ingredient Dictionary, Fifth Edition, 1993, published by CTFA (The Cosmetic, Toiletry & Fragrance Association), incorporated herein by reference.

It is an essential feature of the invention than the benefit agent and surface active agent are separate but combinedly dispensable from a packaging means and typically a single packaging means. Such a packaging means includes those systems which comprise two separate compartments. Ensuring that the surface active agent and benefit agent are separate can be achieved in a variety of ways. Packaging of the composition such that the surface active agent and benefit agent are presented in separate compartments or in separate domains within the packaging; including encapsulation of the benefit agent; and by processing of the composition by coextrusion to produce a striped product in which individual stripes contain either the surface active agent or benefit agent.

A further advantage of the composition according to the invention is that it provides a means whereby benefit agents which are sensitive to surface active agents, i.e. there is a detrimental interaction between the surface active agent and benefit agent, can be used because they are protected from the surface active agent.

Furthermore, the benefit agent may also function as a carrier to deliver efficacy agents to skin treated with the compositions of the invention. This route is particularly useful for delivering efficacy agents which are difficult to deposit onto the skin or those which suffer detrimental interactions with other components in the composition. In such cases the carrier is a often a silicone or hydrocarbon oil which is non solubilised/micellised by the surface active phase and in which the efficacy agent is relatively soluble. Examples of such efficacy agents include anti-viral agents; hydroxycaprylic acids; pyrrolidone; carboxylic acids; 3,4, 4'-trichlorocarbanilide; benzoyl peroxide; perfumes; essential oils; germicides and insect repellants such as 2,4,4'-trichloro-2'-hydroxydiphenyl ether (Irgasan DP300); salicylic acid; willow extract, N,N-dimethyl m-toluamide (DEET); and mixtures thereof.

Compositions of the invention may be formulated as products for washing the skin, for example, bath or shower gels, hand washing compositions or facial washing liquids; pre- and post-shaving products; rinse-off, wipe-off and leave-on skin care products; products for washing the hair and for dental use.

The compositions of the invention will generally be pourable liquids or semi-liquids e.g. pastes and will have a viscosity in the range 250 to 100,000 mPas measured at a shear rate 10s$^{-1}$ and 25° C. in a Haake Rotoviscometer RV20.

When the product is formulated as a shower gel the viscosity will generally be in the range 800 to 15000 mPas measured at a shear rate 10s$^{-1}$ and 25° C.

When the product is formulated as a facial wash product the viscosity will generally be in the range 3000 to 100,000 mPas measured at a shear rate 10s$^{-1}$ and 25° C.

Other typical components of such compositions include opacifiers, preferably 0.2 to 2.0 wt %; preservatives, preferably 0.2 to 2.0 wt % and perfumes, preferably 0.5 to 2.0 wt %.

The invention will be further illustrated by reference to the following non-limiting examples.

EXAMPLES

In the examples:
Behenyl alcohol was Nacol 22-97 ex Condea.
Behenyl silicone wax was Cire 71649 ex Rhone Poulenc.
Coco amidopropyl betaine was Rewoteric AMB14kS ex Rewo (examples I to V) or Amonyl BA 380 ex Seppic.

Cross-linked polyacrylate was Carbopol ETD 2020 ex Goodrich.
Fatty acid monoglyceride polyglycol ether was Rewoderm LIS 80 ex Rewo.
Guar hydroxypropyl trimonium chloride was Jaguar C-13-S ex Meyhall.
IPP (isopropyl palmitate) was Estol 1517 ex Unichema.
Lauryl lactate was Crodamol LL ex Croda Chemicals.
MEA sulphosuccinate was Witco 5690 Ex Witco.
Polyethylene AC617 was from A–C Performance Additives.
Silica was a hydrophobically modified silica, Aerosil R972, ex Degussa.
Silicone oil was DC200, a polydimethylsiloxane ex Dow Corning with a viscosity of 60000 mPas.
Silicone oil emulsion was BC 92/057 ex Basildon.
Sodium cocoyl isethionate was either Jordapon CI ex PPG/Mazer (examples I to V) or Hostapan SCI ex Hoechst.
Sodium lauryl ether sulphate was Genapol ZRO ex Hoechst
Stearic acid was Pristerine 4911 ex Unichema.

Examples I–IV

The following method was used to determine the amount of benefit agent deposited onto full thickness porcine skin. (5×15 cm) treated with compositions according to the invention.

The skin was prehydrated and then 0.5 ml of the product applied to it. The product was lathered for 10 seconds and then rinsed for 10 seconds under running water.

Thereafter the skin was wiped once with a paper towel to remove excess water.

2 minutes after drying a strip of adhesive tape was pressed onto the skin for 30 seconds by applying a constant load of $10 g.cm^{-2}$. The adhesive tape employed was J-Lar Superclear (TM) tape having a width of 2.5 cm. In total ten strips of tape were applied to adjacent sites on the skin.

In this test procedure silicone which has deposited on the skin will subsequently be transferred to the tape along with some of the outer layer of the skin.

The amounts of silicon and skin adhering to the tape are determined by means of X-ray fluorescence spectroscopy. The tape strips are placed in an X-ray fluorescence spectrometer with the adhesive side facing the beam of this machine A mask is applied over the tape to define a standardised area in the middle of the tape which is exposed to the X-ray beam. The sample chamber of the machine is placed under vacuum before making measurements and the spectrometer is then used to measure the quantities of silicon and sulphur. The sulphur is representative of the amount of skin which has transferred to the tape.

The amounts of silicon and sulphur observed with a clean piece of adhesive tape are subtracted from the experimental measurements. The experimental measurements for the average levels of sulphur and silicon are expressed as a ratio of silicon to sulphur. From this ratio it is possible to determine silicone oil deposition per unit area of skin.

Example I

A base facial wash product having the following composition was prepared.

| Base Formulation (A) | wt % |
|---|---|
| Sodium cocoyl isethionate | 7.5 |
| Coco amidopropyl betaine (CAPB) | 3.75 |
| MEA sulphosuccinate | 3.75 |
| Fatty acid monoglyceride polyglycol ether | 3.00 |
| Stearic acid | 3.00 |
| Behenyl alcohol | 3.00 |
| Water + minors | to 100 |

The composition was prepared in a Esco labor (TM) mixer by mixing CAPB, MEA sulphosuccinate, fatty acid monoglyceride polyglycolether and water under vacuum and with heating to temperature in the range 70° to 80° C. Thereafter, sodium cocoyl isethionate was added and the mixture homogenised while maintaining the vacuum and temperature. Stearic acid and behenyl alcohol were then added and the temperature maintained at between 70° and 80° C. until they had both melted. The resulting mixture was then cooled slowly.

The benefit agent used in this example was a silicone oil. The package used in this example was a toothpaste tube of the type described in British Patent 996 377, incorporated herein by reference, used to dispense striped toothpaste products. Such a dispenser comprises a dispensing container and a dispensing orifice. The dispensing container is provided with a central tube which extends from the orifice into the interior of the dispensing container. Base formulation is discharged through this central tube. Axial recesses are provided on the wall of the central tube defining minor passages through which the silicone oil is discharged simultaneously. Silicone oil was put into the package followed by the base formulation such that the total composition in the tube comprised 6 wt % oil and 94 wt % base formulation.

One gram of product was dispensed onto the skin from the tube resulting in stripes of benefit agent and base formulation with the benefit agent forming the outer stripes.

The amount of silicone oil deposited onto the skin was measured as described above. A comparison was carried out with the base formulation (A) i.e. no silicone oil added and with a product of composition (B), below, in which a silicone oil emulsion was mixed with the base formulation before being placed in the toothpaste tube.

| Formulation B | wt % |
|---|---|
| Sodium lauryl ether sulphate | 13.00 |
| Coco amidopropyl betaine (CAPB) | 2.00 |
| Silicone oil emulsion | 5.00 |
| Guar hydroxpropyl trimonium chloride | 0.10 |
| Sorbic acid | 0.37 |
| Sodium citrate dihydrate | 0.49 |
| Sodium chloride# | ~2 |
| Citric acid* | ~0.01 |
| Water + minors | to 100 | level can be varied in order to give the required viscosity
*level can be varied in order to give the required pH The following results were obtained.

| Composition | Deposition (Si/S) |
|---|---|
| I | 90 |
| A | 0.03 |
| B | 1.1 |

The results demonstrate the advantage of the invention in which product is dispensed with stripes of base formulation, comprising the surface active agent, and of silicone oil.

Example II

Example I was repeated, i.e. 1 g of product with the same benefit agent was dispensed from a toothpaste tube used to dispense striped toothpastes, except the amount of thickening agent (fatty acid monoglyceride polyglycol ether) added to the base formulation was varied. In IIA, IIB and IIC the base formulation was the same as that used in example I with the amount of thickening agent being 5, 7.5 and 10 wt % respectively, based on base formulation. Comparisons were carried out with the products containing the base formulation B above with 10 wt % thickening agent but no silicone oil emulsion or guar derivative (composition C) and with the base formulation A.

The following results were obtained:

| Composition | Si:S ratio | Viscosity/mPas 25° C., 10s$^{-1}$ |
| --- | --- | --- |
| A | 0.09 | |
| C | 13.38 | |
| IIA | 37.98 | 13300 |
| IIB | 48.89 | 72890 |
| IIC | 89.73 | 84420 |

As the concentration of thickening agent in the base formulation is increased so deposition of the benefit agent is increased.

Example III

In this example the composition of example I with 10 wt % thickener (fatty acid monoglyceride polyglycol ether) added to the base formulation, was dispensed from a pump action toothpaste dispenser, i.e. a dispenser comprising two tubes physically separated from one another with a common orifice but with separate connections to each tube, of the type described in U.S. Pat. No. 5,020,694 and U.S. Pat. No. 5,038,963, incorporated herein by reference. In the dispenser one tube was filled with silicone oil and the other with the base formulation A of example 1. One gram of silicone oil and base formulation were dispensed at a ratio of 50:50 oil:base. The following results were obtained.

| Package orifice radius/cm | Si:S |
| --- | --- |
| 0.3 | 1658 |
| 0.5 | 3664 |

Example IV

Example III was repeated with the package with the 0.3 cm radius orifice (IV) and compared with deposition from the same package in which a mixture of base formulation and silicone oil were added to both tubes of the dispenser (example D). The ratio of oil to base formulation dispensed from both packages was 50:50. The following results were obtained.

| Package | Si:S |
| --- | --- |
| D | 141 |
| IV | 4702 |

The results demonstrate the advantage, in terms of deposition of silicon, of a striped product over a product in which all the components of the composition are mixed.

Example V

In this example the benefit agent was IPP (isopropyl palmitate). The following method was used to determine the amount of IPP deposited onto full thickness porcine skin (5×15 cm pieces) treated with compositions according to the invention.

The skin was treated and washed with the compositions according to the invention by the same method as described for examples I to IV. Thereafter the skin was extracted with ethanol three times (3 ml per extract), the extract made up to 10 g and submitted for Gas Chromatography analysis to determine the amount of IPP deposited.

Example III was repeated using the package with the 0.5 cm radius orifice with the same base formulation as in example I but with IPP (isopropyl palmitate) as the benefit agent. IPP was thickened with 10 wt % fumed silica.

Deposition of this composition was compared with deposition from the same package in which a mixture of base formulation and IPP were added to both tubes of the dispenser (example E). The ratio of IPP to base formulation dispensed from both packages was 50:50. The following results were obtained.

| Package | Deposition of IPP/ppm |
| --- | --- |
| E | 137 |
| V | 4702 |

The results demonstrate the advantage, in terms of deposition of IPP, of a striped product over a product in which all the components of the composition are mixed.

Example VI

The following method was used to determine the amount of lauryl lactate deposited onto skin treated with compositions according to the invention containing lauryl lactate.

Porcine full thickness skin was prehydrated and then 0.20 g of the product and 0.8 g of water applied to it. The skin was washed for 30 seconds and then rinsed for 10 seconds under running water.

Thereafter the Skin was wiped once with a paper towel to remove excess water.

30 seconds after drying 5 strips of Desquame tape were applied to the skin sequentially for 10 seconds.

The strips were then removed from the skin and hydrolysed in 2 ml of NaOH (0.5M) at 60° C. for 60 minutes. They were then neutralised with 2 ml HCl (0.5M) and in Sorensens phosphate buffer (pH 7.0). The total lauryl lactate and the protein content of the tapes, representative of the lauryl lactate transferred to the skin, was determined using Sigma diagnostic assay Kits 735/10 and 690. A solution containing the assay and treated strips was prepared and the absorbance at 540 nm measured in a uv spectrometer.

The base formulation for the following experiments was:

| | Wt % |
| --- | --- |
| MEA sulphosuccinate | 11.7 |
| Cross-linked polyacrylate | 0.3 |

|  | Wt % |
|---|---|
| Sodium cocoyl isethionate | 8.5 |
| Cocoyl amidopropyl betaine | 15.8 |
| Water & minors | to 100 |

It was prepared by dispersing the polyacrylate in excess water. A premix of the two surfactants was then added to the polymer dispersion. Thereafter minors were added.

The following emollient oil mixtures were used:

|  | Oil mixture | wt % | Droplet size/μm |
|---|---|---|---|
| X | Lauryl lactate | 85 | 172.2 |
|  | Polyethylene AC617 | 15 |  |
| Y | Lauryl lactate | 99 | 183.7 |
|  | Silica | 1 |  |
| Z | Lauryl lactate | 99 | 187.6 |
|  | Behenyl silicone wax | 1 |  |

In one set of experiments to simulate the claimed invention the thickened benefit agent was applied as a stripe to the skin adjacent to a stride of the base formulation. For comparison purposes, a emulsion of the base formulation and thickened benefit agent, was also applied to the skin.

(For Y the emulsion was prepared by mixing the two components at room temperature whereas for X and Z it was necessary to heat the mixture).

The following results were obtained:

|  | Stripe lactate/Absorbance Units ($10^{-3}$) | Emulsion lactate/Absorbance Units ($10^{-3}$) |
|---|---|---|
| Untreated skin | 81 | 81 |
| base formulation | 62 | 63 |
| base + 1%*X | 95 | 69 |
| base + 5%*X | 324 | 128 |
| base + 10%*X | 607 | 154 |
| Untreated skin | 154 | 151 |
| base formulation | 139 | 142 |
| base + 5% lauryl lactate | 169 | 139 |
| base + 5%#Y | 230 | 141 |
| base + 5%#Z | 254 | 158 |

*based on the total composition
-% of lauryl lactate based on total composition The results demonstrate the advantage of a composition in which the base formulation, comprising the surface active agent, and benefit agent are deposited onto the skin in separate domains over a compositions in which the base formulation and benefit agent are in the form of an emulsion.

We claim:

1. An aqueous liquid cleansing and moisturizing composition comprising:
   (a) 50% to 99.9% by wt. of a base formulation comprising 1% to 35% by wt. of a surface active agent selected from the group consisting of anionic, nonionic, zwitterionic and cationic surface active agents, soap and mixtures thereof; and
   (b) 0.1% to 50% by wt. of a benefit agent selected from the group consisting of silicone oils, gums, fats, oils, waxes, hydrophobic plant extracts, hydrocarbons, fatty acids, alcohols, esters, essential oils, lipids, phospholipids, vitamins, sunscreens, and mixtures thereof;

wherein the benefit agent and the base formulation comprising said surface active agent are physically separate such that the base formulation and the benefit agent are not in direct contact with one another but are nonetheless dispensable from a single packing means which comprises both the base formulation and the benefit agent as individual stripes;

wherein each stripe comprises either said benefit agent or said base formulation;

wherein each stripe has a width of at least 1,000 microns; and wherein (a) and (b) are not post mixed prior to use.

2. A composition according to claim 1, wherein the benefit agent additionally comprises 0% to about 10% by weight of a thickening agent.

3. A composition according to claim 1, wherein the base formulation additionally comprises about 5% to 10% by weight of a thickening agent.

4. A method of using a liquid cleansing and moisturizing composition comprising:
   (a) 50% to 99.9% by weight of a base formulation comprising 1% to 35% by weight of a surface active agent selected from the group consisting of anionic, nonionic, zwitterionic and cationic surface active agents, soap and mixtures thereof; and
   (b) 0.1% to 50% by weight of a benefit agent selected from the group consisting of silicone oils, gums, fats, oils, waxes, hydrophobic plant extracts, hydrocarbons, fatty acids, alcohols, esters, essential oils, lipids, phospholipids, vitamins, sunscreens, and mixtures thereof;

wherein said method comprises:
   i) dispensing the base formulation containing said surface active agent and the benefit agent from a packaging means; and
   ii) applying the base formulation and the benefit agent to the human body;

wherein said base formulation and said benefit agent are physically separate such that said base formulation and said benefit agent are not in direct contact with one another but are nonetheless combinedly dispensable from a single packaging means as individual stripes;

wherein each stripe comprises either said benefit agent or said base formulation;

wherein each stripe has a with of at least 1,000 microns; and wherein (a) and (b) are not post mixed prior to use.

5. A method according to claim 4, wherein the additive formulation additionally comprises 0% to about 10 % by weight of a thickening agent.

6. A method of improving the deposition of a benefit agent from a liquid cleansing and moisturizing composition comprising:
   (a) 50% to 99.9% by weight of a base formulation comprising 1% to 35% by weight of a surface active agent selected from the group consisting of anionic, nonionic, zwitterionic and cationic surface active agents, soap and mixtures thereof; and
   (b) 0.1% to 50% by weight of a benefit agent selected from the group consisting of silicone oils, gums, fats, oils, waxes, hydrophobic plant extracts, hydrocarbons, fatty acids, alcohols, esters, essential oils, lipids, phospholipids, vitamins, sunscreens, and mixtures thereof;

wherein said method comprises:
   i) dispensing the base formulation containing said surface active agent and the benefit agent from a packaging means; and ii) applying the base formulation and the benefit agent to the human body;

wherein said base formulation and said benefit agent are physically separate such that said base formulation and said benefit agent are not in direct contact with one another but are nonetheless combinedly dispensable from a single packaging means as individual stripes;

wherein each stripe comprises either said benefit agent or said base formulation;

wherein each stripe has a with of at least 1,000 microns; and wherein (a) and (b) are not post mixed prior to use.

7. A method according to claim 6 wherein the composition is dispensed from a single packaging means.

8. A method according to claim 6, wherein the additive formulation additionally comprises 0% to 10% by weight of a thickening agent.

* * * * *